United States Patent
Kelley et al.

(10) Patent No.: US 10,301,666 B2
(45) Date of Patent: May 28, 2019

(54) DIAGNOSTIC AND SAMPLE PREPARATION DEVICES AND METHODS

(71) Applicant: General Atomics, San Diego, CA (US)

(72) Inventors: Shana O. Kelley, Toronto (CA); Susan Bortolin, Oakville (CA); Reginald James McKenzie Orton, Toronto (CA); Stefan Christopher Wiechula, Toronto (CA)

(73) Assignee: General Atomics, San Diego, CA (US)

( * ) Notice: Subject to any disclaimer, the term of this patent is extended or adjusted under 35 U.S.C. 154(b) by 105 days.

(21) Appl. No.: 15/408,225

(22) Filed: Jan. 17, 2017

(65) Prior Publication Data

US 2017/0253912 A1   Sep. 7, 2017

Related U.S. Application Data

(62) Division of application No. 14/003,709, filed as application No. PCT/US2012/028721 on Mar. 12, 2012, now Pat. No. 9,580,742.

(60) Provisional application No. 61/451,528, filed on Mar. 10, 2011.

(51) Int. Cl.
| | |
|---|---|
| *C12Q 1/6816* | (2018.01) |
| *C12Q 1/6806* | (2018.01) |
| *C12N 1/06* | (2006.01) |
| *C12N 13/00* | (2006.01) |
| *C12N 15/10* | (2006.01) |

(52) U.S. Cl.
CPC .......... *C12Q 1/6806* (2013.01); *C12N 1/066* (2013.01); *C12N 13/00* (2013.01); *C12N 15/1003* (2013.01); *C12Q 1/6816* (2013.01)

(58) Field of Classification Search
None
See application file for complete search history.

(56) References Cited

U.S. PATENT DOCUMENTS

| | | | |
|---|---|---|---|
| 5,312,527 | A | 5/1994 | Michelsen et al. |
| 5,874,046 | A | 2/1999 | Megerle |
| 5,968,745 | A | 10/1999 | Thorp et al. |
| 5,972,692 | A | 10/1999 | Hashimoto et al. |
| 6,123,819 | A | 9/2000 | Peeters |
| 6,180,346 | B1 | 1/2001 | Thorp et al. |

(Continued)

FOREIGN PATENT DOCUMENTS

| | | |
|---|---|---|
| AU | 758 063 | 3/2003 |
| CN | 101306794 | 11/2008 |

(Continued)

OTHER PUBLICATIONS

Bahi et al., "Electroporation and lysis of marine microalga *Karenia brevis* for RNA extraction and amplification," Journal of the Royal Society Interface, 22(3): 68-608 (2010).

(Continued)

*Primary Examiner* — Robert T. Crow

(57) ABSTRACT

Contemplated methods and devices are drawn to preparation and analysis of analytes from biological samples. In a preferred embodiment the analytes are nucleic acids that are both released from biological compartments present in the sample and fragmented through the use of a voltage potential applied to a pair of electrodes. The nucleic acids thus prepared are subsequently characterized.

9 Claims, 15 Drawing Sheets

(56) References Cited

U.S. PATENT DOCUMENTS

| | | | |
|---|---|---|---|
| 6,221,586 B1 | 4/2001 | Barton et al. | |
| 6,325,904 B1 | 12/2001 | Peeters | |
| 6,361,951 B1 | 3/2002 | Thorp et al. | |
| 6,399,303 B1 | 6/2002 | Connolly | |
| 6,479,240 B1 | 11/2002 | Kayyem et al. | |
| 6,593,090 B2 | 7/2003 | Connolly | |
| 6,664,104 B2 | 12/2003 | Pourahmadi et al. | |
| 7,202,028 B2 | 4/2007 | Thorp et al. | |
| 7,361,470 B2 | 4/2008 | Kelley et al. | |
| 7,361,471 B2 | 4/2008 | Gerdes et al. | |
| 7,741,033 B2 | 6/2010 | Kelley et al. | |
| 8,283,155 B2 | 10/2012 | Holmes | |
| 9,580,742 B2 | 2/2017 | Kelly et al. | |
| 2002/0081588 A1 | 6/2002 | De Lumley-woodyear et al. | |
| 2002/0084410 A1 | 7/2002 | Colbert et al. | |
| 2002/0158342 A1 | 10/2002 | Tuominen et al. | |
| 2003/0087277 A1 | 5/2003 | Fritzsche et al. | |
| 2003/0089899 A1 | 5/2003 | Lieber et al. | |
| 2003/0143571 A1 | 7/2003 | Sharp et al. | |
| 2003/0211637 A1 | 11/2003 | Schoeniger et al. | |
| 2004/0011650 A1 | 1/2004 | Zenhausern et al. | |
| 2004/0022677 A1 | 2/2004 | Wohlstadter et al. | |
| 2004/0040840 A1 | 3/2004 | Mao et al. | |
| 2004/0072263 A1 | 4/2004 | Link et al. | |
| 2004/0106203 A1 | 6/2004 | Stasiak et al. | |
| 2004/0114445 A1 | 6/2004 | Occhipinti et al. | |
| 2004/0136866 A1 | 7/2004 | Pontis et al. | |
| 2005/0084881 A1 | 4/2005 | Kelly et al. | |
| 2005/0142663 A1 | 6/2005 | Parthasarathy et al. | |
| 2005/0211559 A1* | 9/2005 | Kayyem | B01L 3/5027 204/601 |
| 2005/0239121 A1 | 10/2005 | Gall et al. | |
| 2006/0216812 A1 | 9/2006 | Okada et al. | |
| 2007/0141605 A1 | 6/2007 | Vann | |
| 2007/0231217 A1 | 10/2007 | Clinton et al. | |
| 2008/0138886 A1 | 6/2008 | Murphy | |
| 2009/0035746 A1 | 2/2009 | Ehben et al. | |
| 2009/0137029 A1* | 5/2009 | Breidenthal | B01F 11/0045 435/287.2 |
| 2009/0214391 A1 | 8/2009 | Scurati | |
| 2009/0270266 A1 | 10/2009 | Kelley et al. | |
| 2009/0294305 A1* | 12/2009 | Bekki | G01N 33/5438 205/792 |
| 2009/0308744 A1 | 12/2009 | Nam et al. | |
| 2010/0041077 A1 | 2/2010 | Nagy et al. | |
| 2010/0112667 A1 | 5/2010 | Sundaram et al. | |
| 2010/0129878 A1 | 5/2010 | Parthasarathy et al. | |
| 2011/0156804 A1 | 6/2011 | Pelgrom et al. | |
| 2011/0224098 A1 | 9/2011 | Luan et al. | |
| 2011/0233075 A1 | 9/2011 | Soleymani et al. | |
| 2014/0072962 A1 | 3/2014 | Kelley | |
| 2014/0087375 A1 | 3/2014 | Kelley et al. | |
| 2015/0044679 A1 | 2/2015 | Jack | |
| 2017/0253912 A1* | 9/2017 | Kelley | C12N 1/066 |

FOREIGN PATENT DOCUMENTS

| | | |
|---|---|---|
| EP | 0 564 254 | 10/1993 |
| EP | 1629122 | 3/2006 |
| EP | 1784512 | 5/2007 |
| EP | 2163653 | 3/2010 |
| GB | 2 416 030 B | 1/2006 |
| JP | 10-267888 | 10/1998 |
| JP | 2003-322653 | 11/2003 |
| JP | 2005227145 | 8/2005 |
| JP | 2006-030027 | 2/2006 |
| JP | 2007-187531 | 7/2007 |
| WO | WO 92/17774 | 10/1992 |
| WO | WO 96/06946 | 3/1996 |
| WO | WO 99/67628 | 12/1999 |
| WO | WO 02/074988 | 9/2002 |
| WO | WO 02/079514 | 10/2002 |
| WO | WO 2003/049592 | 6/2003 |
| WO | WO 2004/027093 | 4/2004 |
| WO | WO 2005/073691 | 8/2005 |
| WO | WO 2005/083078 | 9/2005 |
| WO | WO 05/005952 | 10/2005 |
| WO | WO 06/076047 | 7/2006 |
| WO | WO 06/094200 | 9/2006 |
| WO | WO 2007/094805 | 8/2007 |
| WO | WO-2009018473 A1 * | 2/2009 ......... A61B 10/0096 |
| WO | WO 2010/025547 | 3/2010 |
| WO | WO 2011/119711 A1 | 9/2011 |
| WO | WO 2012/109157 | 8/2012 |
| WO | WO 2012/122564 | 9/2012 |

OTHER PUBLICATIONS

Das et al., "A Nanocatalyst-Based Assay for Proteins: DNA-Free Ultrasensitive Electrochemical Detection Using Catalytic Reduction of p-Nitrophenol by Gold-Nanoparticle Labels," Journal of the American Chemical Society, vol. 128, No. 50, pp. 10622-16023 (2006).

De La Rosa et al., "Microfluidic Device for Dielectrophoresis Manipulation and Eletrodisruption of Respiratory Pathogen *Bordatella pertussis*," IEEE Transactions on Biomedical Engineering, 55(10): 2426-2432 (2008).

Di Carlo et al., On-chip cell lysis by local hydroxide generation, Lab on a Chip, 5(2): 171-178 (2005).

genome.gov [retrieved on Feb. 22, 2016], retrieved from the Internet: <URL: www.genome.gov/11006943.

International Search Report and Written Opinion of the International Searching Authority of International Application No. PCT/US2012/020965, dated Aug. 28, 2012.

International Search report and Written Opinion of the International Searching Authority of International Application No. PCT/US2012/024015, dated Jul. 13, 2012.

International Search report and Written Opinion of the International Searching Authority of International Application No. PCT/US2012/028721, dated Oct. 31, 2012.

International Search report and Written Opinion of the International Searching Authority of International Application No. PCT/US2005/27710, dated Feb. 22, 2006.

International Search report and Written Opinion of the International Searching Authority of International Application No. PCT/US2013/054395, dated Oct. 12, 2013.

International Search report and Written Opinion of the International Searching Authority of International Application No. PCT/IB2014/002529, dated Mar. 19, 2015.

Kelly et al., "Single-base mismatch detection based on charge transduction through DNA," Nucleic Acid Research, 27(24): 4830-4837 (1999).

Kim et al., "Microfluidic Sample Preparation: Cell Lysis and Nucleic Acid Purification," Integrative Biology, vol. 1, No. 10, pp. 574-586 (Aug. 25, 2009).

Lam et al., "Polymerase Chain Reaction-Free, Sample-to-Answer Bacterial Detection in 30 Minutes with Integrated Cell Lysis," Analytical Chemistry, vol. 84, No. 1, pp. 21-25 (Dec. 5, 2011).

Lee et al., "Electrochemical cell lysis device for DNA extraction," Lab on a Chip, 10(5): 626-633 (2010).

Liao et al., "Use of Electrochemical DNA Biosensors for Rapid Molecular Identification of Uropathogens in Clinical Urine Specimens," Journal of Clinical Microbiology, 44(2): 561-570 (2006).

Lu et al., Three Dimensional Electrode Array for Cell Lysis Via electroporation, Biosensors and Bioelectronics, vol. 22, No. 4, pp. 568-574 (Sep. 25, 2006).

Martin et al., "Nanomaterials in Analytical Chemistry," Analytical Chemistry News and Features, pp. 322A-327A (1998).

Matysik, "Miniaturization of Electroanalytical Systems," Anal. Boanal. Chem. 375(a): 33-35 (2003).

Pan et al., "Electrochemical Immunosensor Detection of Urinary Lactogerrin in Clinical Samples for Urinary Tract Infection Diagnosis," Biosensors and Bioelectronics, vol. 26, No. 2, pp. 649-654 (Jul. 8, 2010).

Supplementary European Search Report for EP 12754295.9, dated Oct. 29, 2014.

(56) References Cited

OTHER PUBLICATIONS

Tomioka et al., "A multiplex Polymerase Chain Reaction microarray Assay to Detect Bioterror Pathogens in Blood," The Journal of Molecular Diagnostics, vol. 7, No. 4, pp. 486-494 (Oct. 2005).
Wang et al., "A Microfluidic Flow-Through Device for High Throughput electrical Lysis of Bacterial Cells Based on Continuous De Voltage," Biosensors and Bioelectronics, vol. 22, No. 5, pp. 582-588 (Mar. 10, 2006).
West et al., "Accessing DNA by Low Voltage Alternating Current Joule Effect Heating," Analytical Chimica Acta, vol. 527, pp. 1-12 (Oct. 7, 2004).
Wink et al., "Self-assembled monolayers for biosensors," Analyst, 112(4): 43R-50R (1997).
Xiao et al., "Label-free Electrochemical detection of DNA in blood serum via target-induced resolution of an electrode-bound DNA pseudoknot," J. Am. Chem. Soc., 129(30): 11896-11897.

\* cited by examiner

DIAGNOSTIC AND SAMPLE PREPARATION DEVICES AND METHODS

This application is a division of U.S. patent application Ser. No. 14/003,709, filed Dec. 13, 2013, now U.S. Pat. No. 9,580,742, which is a U.S. National Stage Application filing under 35 U.S.C. 371 of International Application No. PCT/US2012/028721, filed on Mar. 12, 2012, which claims priority to and the benefit of U.S. Provisional Patent Application No. 61/451,528, filed Mar. 10, 2011, each of which is hereby incorporated by reference herein in its entirety.

FIELD OF THE INVENTION

The field of the invention is compositions and methods related to nucleic acid preparation and analysis, particularly as they relate to point of care diagnostic devices and methods.

BACKGROUND

Characterization of analytes found in biological samples is an integral part of both biological research and medical practice. Preparation of samples is a common first step in this process, and varies considerably in complexity depending on the nature of the analyte and the biological sample itself. For determination of the concentration of a therapeutic drug in plasma, sample preparation can be as simple as waiting for a clot to form and transferring a portion of the liquid fraction to an analyzer. Other analytes, such as nucleic acids, may normally be sequestered inside of cells or viruses from which they need to be released prior to characterization. In addition, once released it is often desirable to process such molecules further in order to simplify analysis.

Numerous methods are known for releasing analyte molecules from cells, including mechanical approaches (such as sonication, application of shear forces, application of heat and agitation in the presence of particles) and chemical methods (such as the use of heat (to produce chemical effect), surfactants, chaotropes, and enzymes). Some of these have been adapted for use in cartridge or microfluidics-based platforms such as those represented by single use in-office and point-of-care testing devices and, increasingly, as components of complex systems where contamination is a concern. For example, U.S. Pat. No. 5,874,046A discloses cell disruption through the use of ultrasonics and application of shear forces, among other methods. Similarly, GB2416030B discloses integrated devices that utilizes mechanical or enzymatic digestion to lyse cells and release their contents for analysis. U.S. Pat. No. 6,664,104B2 discloses devices that lyse cells by a variety of means including mechanical disruption, the application of ultrasound, and the addition of chaotropes to the sample. WO2011/119711A1 discloses an assay cartridge that utilizes elevated temperatures and pressures as a sample treatment to release analytes from such biological compartments. Unfortunately, mechanical methods for cell disruption can add significantly to the complexity of an integrated device and the supporting instrumentation. Similarly, addition of chemical reagents such as chaotropes or enzymes, to a sample not only require a means for metering the correct amount of reagent but may require removal of such reagents at a later point in the process lest they complicate analysis. This is particularly true for sensitive analytical methods such as PCR or electrochemistry.

Although it is often used for introduction of foreign genetic material into cells, electroporation has been shown to be an effective means for the release of nucleic acids from cells. Release of nucleic acids from algal cells has been disclosed (Bahi et al, *J. R. Soc. Interface*, 8:601-608 (2011)), by initially concentrating the cells on an electrode surface and applying a high frequency (600 kHz) current. Unfortunately, such conditions can lead to the production of considerable heat, which may be difficult to dissipate from a microfluidics device without the use of complex heat exchangers or other thermal transfer devices. US2010/0112667A1 discloses the use of a device with a complex electrode configuration that places numerous small insulators placed between a pair of electrodes in order to lyse cells; this configuration generates high current field gradients within the small gaps between the insulators and reduces power requirements. These conditions can also cause other undesirable effects such as bubbles, increased reactive or inhibiting agents, or breakdown of the supporting structures.

Lysis of eukaryotic cells by generation of hydrolysis products within a microfluidic device using electrodes has also been described (Di Carlo et al, Lab Chip, 5:171-178 (2005), wherein local generation of hydroxide ions at relatively high concentrations (estimated at approximately 20 mM) were found to be necessary for rapid lysis. These investigators did not report on recovery or characterization of analytes from the lysed cells. Lee et al (Lab Chip, 10:626-633 (2010)) describe a similar device that incorporates an ion exchange polymer diaphragm to generate high hydroxide concentrations in order to effectively lyse bacterial cells. The authors were able to perform PCR on DNA analytes released in this process but noted that this general approach was not suitable for use with RNA and PCR based detection techniques.

Overall, current methods for release of analytes from cells, viruses, and other biological compartments are difficult to implement in a self-contained microfluidic or point-of-care device. The relatively small size of such devices leads to volume restrictions that complicate operations such as fluid handling related to reagent addition and solid phase capture and release of analytes in order to remove such added reagents prior to analysis. Their reduced dimension also limit options for applying physical forces (such as ultrasound and shear forces) using conventional equipment and provide relatively little heat capacity to control temperature. While electrode-based methods such as electrochemical generation of reactive species have been used, their utility with certain analytes, notably RNA, is unclear. None of these approaches provides controlled analyte fragmentation, which is advantageous in many direct analytical methods, in addition to biological compartment lysis.

The above show that there is an unmet need for a method and device that not only provides reliable, rapid, easily controlled biological compartment lysis and fragmentation of the analytes thus released, but also has simple hardware requirements that are readily adaptable to small scale devices. Such a device and method may be incorporated into a microfluidic "lab on a chip" or point-of-care device where controlled cell lysis and analyte fragmentation has utility.

SUMMARY OF THE INVENTION

A modulated electrical potential applied to a set of electrodes was used to release nucleic acids, and especially RNA, from a biological sample, with the aim of providing a simple and reliable approach to genetic analysis that was amenable to miniaturization and use in in-office, point-of-care devices. Surprisingly, it was found that control of various aspects of the modulated electrical potential permitted both release of nucleic acids from biological samples and controlled fragmentation of the released nucleic acids (typically RNA). The observed fragmentation is achieved rapidly at low voltages, and advantageously reduces the time required for analysis as well as heat generation, reduced bubbles and a reduction in the unwanted chemical byproducts. Moreover, such systems and methods are especially desirable where downstream analysis is a direct electrochemical RNA hybridization analysis.

In one embodiment of the inventive subject matter, a biological sample or a portion thereof is placed in an extraction zone that includes a pair or multiple pairs of electrodes. A modulated potential difference is applied to the electrodes, which induces release of nucleic acids, and especially RNA, from the biological sample and into solution. The released nucleic acids are fragmented while in the extraction zone, with the average length of the fragmented nucleic acids being equal to or less than about 75% (more preferably equal to or less than about 50%, and most preferably equal to or less than about 25%) of the length of the released nucleic acids prior to fragmentation. The method may have an additional step of adjusting the modulated potential difference, the residency time of the biological sample in the extraction zone, or both in order to adjust the average length of the nucleic acid fragments. The modulated potential difference may be adjusted in a variety of ways, including but not limited to the magnitude of the voltage applied to the electrodes, the duration of a voltage pulse applied to the electrodes, and the frequency at which a voltage pulse is applied to the electrodes, or a combination of these. In other embodiments, the average length of the nucleic acid fragments may be about 200 bases in length or less. In still other embodiments, the modulated potential difference is controlled to produce nucleic acid fragments that have a reduced time required for hybridization to a solid-phase probe relative to the time required for the nucleic acids to hybridize prior to fragmentation. In such embodiments the time required for hybridization of the nucleic acid fragments may be reduced to at least half the time required for the nucleic acids prior to fragmentation. Reagents may be introduced to the extraction zone to improve the efficiency of these processes, such enhancing reagents can include metal ions, compounds that promote the formation of free radicals, chaotropes, and ionic and nonionic detergents.

Another embodiment of the inventive subject matter is a device for preparation of nucleic acids, and especially RNA, from a biological sample. Such a device may include a fluid reservoir, a sample receiving zone, and an extraction zone. These may be arranged such that the sample receiving zone lies between the fluid reservoir and the extraction zone and is in fluid communication with each, thereby providing a path for fluids from the fluid reservoir, through the sample receiving zone, and into the extraction zone. In such an embodiment, the fluid reservoir can optionally have a pliant wall with an external surface, which may be accessible, and the extraction zone can include a pair or multiple pairs of electrodes. The electrodes of the extraction zone may be configured to both effect the release of nucleic acids from the biological sample and to fragment the released nucleic acids. In some embodiments, the fluid reservoir may include an extraction buffer that supports the preparation of nucleic acids from the biological sample. In some embodiments, pressure applied to the pliant wall of the fluid reservoir displaces or deforms the pliant wall into the fluid reservoir, reducing its volume. In such an embodiment, pressure applied to the fluid reservoir causes the fluid stored within to flow into the sample receiving zone. Such pressure may be applied to the external surface of the pliant wall, and may be applied by a device or manually by a user. Biological samples are frequently supplied in the form of a collecting device, for example a swab. The sample receiving zone may be configured to receive and retain such a sample and at least a portion of the attendant collecting device.

In another embodiment of the inventive subject matter, a biological sample is analyzed using a device with an extraction zone that includes a pair or multiple pairs of electrodes and is in fluid communication with an analysis zone that includes a sensing electrode and a reference electrode. A portion of the biological sample is introduced into the extraction zone, where a charge or current is applied to the electrodes therein using a protocol that is effective in releasing nucleic acids, and especially RNA, from the biological sample and fragmenting the released nucleic acids to produce fragmented nucleic acids. These fragments can have an average length of about 200 bases or less. The fragmented nucleic acids are moved to the analysis zone, where a second charge or current flow has been applied to the sensing electrode and the reference electrode. A third charge or current flow is then measured between the sensing electrode and the reference electrode to quantify, ascertain the presence of, or otherwise characterize a nucleic acid in the biological sample. In some embodiments, the method includes the use of a sensing electrode that includes a reporting system that is responsive to nucleic acid hybridization. The sensing electrode may include a probe molecule that is at least partially complementary to a fragmented nucleic acid. In some embodiments, the sensing electrode may be nanostructured, such that the nanostructure is spiky, rough, or fractal. Hybridization time is in part dependent upon the size of the nucleic acid fragments; it is thus advantageous to control the size of these fragments. Towards that end, in some embodiments, the first charge or current flow may be adjusted or modulated to optimize or adjust the length of the nucleic acid fragments produced in the extraction zone. Such adjustments can include the magnitude of the voltage applied to the pair of electrodes, the duration of a voltage pulse applied to the pair of electrodes, the frequency at which a voltage pulse is applied to the pair of electrodes, the duration of the treatment time or a combination of these. In other embodiments, the size of the nucleic acid fragments may be optimized or adjusted by controlling residency time of the biological sample within the extraction zone. In still other embodiments, both the first charge or current flow to the pair of electrodes and the residency time of the biological sample within the extraction zone are adjusted to optimize or adjust the size of the nucleic acid fragments.

Thus, the present inventive subject matter provides for the processing of a biological sample to release and provide nucleic acids, and especially RNA, in a form suitable for direct analysis. The inventive subject matter presented herein also provides methods and devices to fragment these nucleic acids in a controlled fashion in order to advantageously reduce the time required for subsequent analysis. These methods and devices are particularly suitable for incorporation into point-of-care devices and microfluidic devices.

Various objects, features, aspects and advantages of the present invention will become more apparent from the following detailed description of preferred embodiments of the invention.

BRIEF DESCRIPTION OF THE DRAWINGS

FIG. 14 illustrates results of the disclosed method.

DETAILED DESCRIPTION

Figure 1:
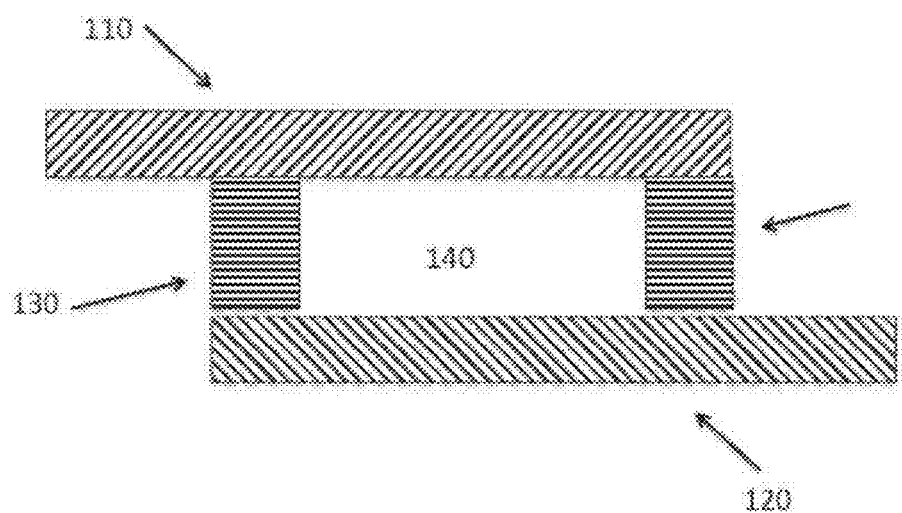
FIG. 1 schematically depicts an embodiment of an extraction zone of the inventive subject matter. A pair of electrodes separated by insulators are exposed within a reaction space, effecting both cell lysis that releases nucleic acids and controlled fragmentation of the nucleic acids thus released.

The inventors have discovered that a modulated potential difference applied to an electrode pair, or applied independently to a series of pairs, may be used to both release nucleic acids, and especially RNA, from a biological sample into solution and also fragment the released nucleic acids in a controlled manner. Release of nucleic acids from biological compartments such as cells, viruses, spores, and so on into free solution is necessary prior to characterization by most current detection methods, particularly those that rely on hybridization to identify specific base sequences. Many of these direct analytical methods also benefit from fragmentation of the native nucleic acid, and especially RNA, as this increases the rate of diffusion and speeds the kinetics of sequence specific hybridization. The inventive subject matter advantageously supports both of these functions in a single preparation area and single processing step, minimizing material losses and greatly simplifying, and reducing time required for, both workflow and the design of devices that incorporate it. In contrast to chemical and enzymatic means for releasing and fragmenting nucleic acids, the applied potential difference is readily controllable. In addition, the inventive subject matter is compatible with known nucleic acid characterization methods, for example electrochemical detection, which may therefore be readily integrated into the same process or device. While the inventive subject matter may be embodied in a variety of devices, its simplicity and minimal hardware requirements make it particularly suitable for use in compact point-of-care devices or microfluidic devices, advantageously permitting the performance of complex genetic characterization on site in a physician's office or in the field.

As used herein, the term "lysis" refers to the process of disrupting the integrity of a biological compartment such as a eukaryotic cell, fungus, bacteria, virus, or spore to such an extent that internal components, and especially RNA, are exposed to and may enter the external environment. Examples of lysis include the formation of permanent or temporary openings in a cell membrane and complete disruption of the cell membrane, both of which permit release of cell contents into the surrounding solution.

As used herein, the term "analyte" refers to a molecule of interest that a user wishes to characterize, quantify, or verify the presence of. Examples of nucleic acid analytes, and especially ribonucleic acid analytes, include messenger RNA (mRNA), ribosomal RNA (rRNA), microRNA (miRNA), non-coding RNA, small interfering RNA (siRNA), and transfer RNA (tRNA). Other analytes include DNA, proteins, carbohydrates, and lipids. Still other examples of analytes include low molecular weight metabolites such as amino acids, nucleotides, and steroids.

As used herein, the term "biological compartment" refers to a discrete structure that contains and segregates biological molecules of interest from the surrounding environment, which is typically a liquid media. Examples of biological compartments include, but are not limited to, eukaryotic cells, fungal cells, bacterial cells, spores, pollen, organelles, liposomes, and viruses.

In one embodiment of the inventive subject matter, lysis is performed by application of a potential difference to a pair of electrodes that are in electrical contact with a volume of fluid containing a biological sample which can contain analytes within a eukaryotic cell, fungus, bacteria, virus, spore, pollen, or other biological compartment. Application of a modulated potential difference to these electrodes, hereafter referred to as lysis electrodes, results in lysis of the biological compartments and subsequent release of analyte into the surrounding solution. The potential difference may be modulated in a variety of ways in order to induce lysis of biological compartments from a sample. In some embodiments, a voltage ranging from about 0.5V to about 3,000V may be applied to the electrodes used for lysis. In a preferred embodiment the voltage applied to the lysis electrodes is about 40V. This voltage may be constant or may be applied in pulses. The duration of such voltage pulses can be up to 60 seconds. In a preferred embodiment the duration of a voltage pulse is about 10 milliseconds. The time between such voltage pulses can be up to 360 seconds. In a preferred embodiment, the time between voltage pulses is about 1 second. A voltage pulse can also have a characteristic waveform, and may be applied to the lysis electrodes as a repeating waveform. Voltage waveforms include, but are not limited to, triangle waves, square waves, sine waves, exponential decaying waves, forward saw tooth waveforms, and reverse saw tooth waveforms. In a preferred embodiment the voltage pulse is applied to the lysis electrodes as a square wave. The mechanism for lysis in this fashion is not known. While not wishing to be bound to any particular theory or hypothesis, the inventor contemplated that lysis is a result of electrolytic processes (for example generation of hydroxide and other reactive species) possibly in concert with electroporation. However the use of relatively low frequency, low voltage potentials, and effectiveness in the presence of buffering species indicates that other mechanisms may be responsible.

In some embodiments of the inventive subject matter, lysis is selective, effecting release of analytes from a subset of cells or other biological compartments present within the biological sample. For example, in such an embodiment, conditions may be selected to lyse and release analyte from epithelial cells present in a cheek swab, but not bacterial cells that are also present in the sample. Selective lysis may be achieved by controlling the voltage that is applied to the lysis electrodes, which may range from about 0.5V to about 3,000V. In other embodiments the duration of a voltage pulse that is applied to the lysis electrodes may be controlled to achieve selective lysis; in such embodiments the duration of the voltage pulse (i.e., the "pulse width") can range from about 1 millisecond to about 60 seconds. In another embodiment selective lysis can be implemented by controlling the frequency at which voltage is applied to the lysis electrodes; in such embodiments this frequency can range from about 0.01 Hz to about 1,000 Hz. In yet another embodiment, high frequency AC potential, which can range from about 0.1 Hz to about 1,000 Hz can be applied to the lysis electrodes in order to effect selective lysis. In still another embodiment, the duration of lysis treatment may be controlled in order to selectively lyse certain cell or other biological compartment types. In such an embodiment the duration of lysis treatment may range from about 1 millisecond to about 5 minutes. In a preferred embodiment two or more of applied voltage, pulse width, voltage frequency, high frequency AC potential, and duration of treatment are controlled in order to perform selective lysis.

In some embodiments of the inventive subject matter, selective lysis is performed without the necessity of modulating the potential applied to the lysis electrodes. In such embodiments, selective lysis may be achieved through the addition of a lysis enhancing probe or sensitizer that associates with a selected biological compartment type. Alternatively, a lysis depreciating or inhibiting probe or desensitizer that associates with selected biological compartment types may be used to effect negative selection. In other embodiments select biological compartments may be segregated prior to lysis, for example by electrophoretic or dielectrophoretic movement, magnetic capture using magnetic particles and capture magnets, antibody-based capture mechanisms, size-selective mechanical filtration, and flow-based particle separation mechanisms. In still other embodiments modulation of the potential applied to the lysis electrodes may be used in combination with the use of one or more of a lysis enhancing probe, a lysis depreciating or inhibiting probe, or a segregation method in order to provide selective lysis.

The efficiency of lysis of biological compartments may be improved by the addition of enhancing reagents to the sample. The enhancing reagent can be, but not limited to, a metal ion, including iron, ruthenium, zinc, manganese, and/or copper ions. These metal ions may be used in combination with chelating agents (e.g., EDTA). In some embodiments, the enhancing reagent is a compound that supports the formation of free radicals. Examples of such compounds include, but are not limited to, chelating agents (e.g., EDTA), hydrogen peroxide, organic peroxides, and dissolved oxygen. In another embodiment, the enhancing reagent is a chaotropic salt. In yet another embodiment, the enhancing reagent is a surfactant, including nonionic detergents and ionic detergents. In some embodiments, two or more enhancing reagents may be used in combination.

Once lysis is effected, a variety of analytes may be released into the surrounding media for further analysis. In a preferred embodiment, the analyte is a nucleic acid.

Examples of nucleic acids include DNA, and especially RNA (e.g., rRNA, mRNA, tRNA, microRNA, noncoding RNA, etc.). Other intracellular analytes, such as proteins (including but not limited to enzymes, structural proteins, regulatory proteins, cell-surface receptors, and immunoglobulins) may be released in this manner. Similarly, low molecular weight intracellular analytes (e.g., nucleotides, hormones, signaling molecules, amino acids, salts, lipids, and steroids) may be released for analysis.

Surprisingly, it was found that, in some embodiments of the inventive subject matter, analyte molecules that are released from the biological compartments are cleaved or fragmented. For example, RNA from a cell lysed by the application of a modulated potential to a pair of lysis electrodes may have an average length of over 2,000 bases immediately upon lysis, but are rapidly cleaved into fragments of reduced length under lytic conditions. The average size of such fragments may be up to about 75% of the size or length of the unfragmented analyte. In other embodiments the average size of such fragments may be up to 60%, up to 50%, up to 40%, up to 30%, or up to 20% of the size or length of the unfragmented analyte. Thus, in a preferred embodiment, the analyte is a nucleic acid (and most typically RNA) where a high proportion of the fragmented nucleic acid is about ≤500 bases, more preferably ≤300 bases, and most preferably ≤200 bases (e.g., between 20 and 100 bases, or between 50 and 150 bases) in length. This fragmentation can advantageously reduce the time required to detect or otherwise characterize the released analyte. For example, fragmentation of an analyte molecule may reduce molecular weight and increase speed of diffusion, thereby enhancing molecular collision and reaction rates. In another example, fragmenting a nucleic acid may reduce the degree of secondary structure, thereby enhancing the rate of hybridization to a complementary probe molecule. The mechanism for this fragmentation is unclear. It is thought to be a result of electrolytic processes (for example generation of hydroxide, free radicals, and other reactive species), however its effectiveness when relatively low frequency, low voltage potentials are used and in the presence of buffering species indicates that other mechanisms may be responsible.

Thus, and viewed from another perspective, fragmentation is preferably adjusted such that subsequent hybridization times are reduced (as compared to hybridization times for unfragmented nucleic acids under otherwise identical conditions) by at least 25%, more preferably at least 50%, even more preferably at least 65%, and most preferably at least 80%. For example, RNA may be released from a cell and fragmented such that the time required for hybridization and electrochemical analysis hybridization times is reduced by at least 25%, more preferably at least 50%, even more preferably at least 65%, and most preferably at least 80%.

In some embodiments of the inventive subject matter, fragmentation of the analyte may be controlled by application of a modulated potential difference to the lysis electrodes. The potential difference may be modulated in a variety of ways. In some embodiments a voltage ranging from about 0.5V to about 3,000V may be applied to the lysis electrodes. In a preferred embodiment, the voltage applied to the lysis electrodes is about 100V, or about 200V from peak voltage to peak voltage. This voltage may constant or may be applied in pulses. The duration of such voltage pulses can be up to 60 seconds. In a preferred embodiment the duration of a voltage pulse is about 10 milliseconds. The time between such voltage pulses can be up to 360 seconds. In a preferred embodiment, the time between voltage pulses is about 1 second. A voltage pulse can also have a characteristic waveform, and may be applied to the lysis electrodes as a repeating waveform. Voltage waveforms include, but are not limited to, triangle waves, square waves, sine waves, exponential decaying waves, forward sawtooth waveforms, and reverse sawtooth waveforms. In a preferred embodiment, the voltage pulse is applied to the lysis electrodes as a square wave. In still another embodiment, the duration of lysis/fragmentation treatment may be controlled in order to control the fragmentation of the analyte. In such an embodiment, the duration of lysis/fragmentation treatment may range from about 1 millisecond to about 5 minutes. Where the treatment time is the time the fluid is in contact with the electrodes. In a continuous flow device, the total time of lysis for a given sample may be greater than the treatment times indicated. In some embodiments of the inventive subject matter, the potential applied to the lysis electrodes for the lysis of biological compartments and for fragmentation of analytes is modulated in the same manner, such that lysis and fragmentation occur within the same time frame. In other embodiments, the potential applied to the lysis electrodes is initially modulated to optimize lysis, and then subsequently modulated to optimize fragmentation of the analyte. In yet another embodiment, modulated voltages that are optimal for biocompartment lysis and for analyte fragmentation may be alternated.

In some embodiments of the inventive subject matter, the lysis electrodes comprise a first electrode and a second electrode separated by a distance which can range from 1 nanometer to 2 millimeters. This space can contain an insulating material so as to further localize the applied potential difference to the electrodes. Lysis electrodes may be constructed of a variety of materials as suits the needs of the manufacturer or application. Suitable materials include carbon and metals such as gold, silver, platinum, palladium, copper, nickel, aluminum, rhuthenium, and alloys thereof. Suitable materials for lysis electrodes may also include conductive polymers, including, but not limited to iodine-doped trans-polyacetylene, poly(dioctyl-bithiophene), polyaniline, metal impregnated polymers and fluoropolymers, carbon impregnated polymers and fluoropolymers, and admixtures thereof. In some embodiments the lysis electrodes may be made, in whole or in part, of a combination of these materials.

Figure 2:
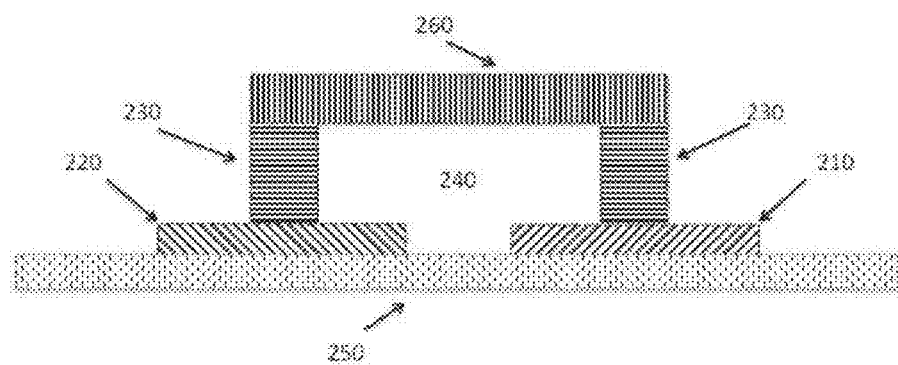
FIG. 2 schematically depicts another embodiment of an extraction zone of the inventive subject matter. A pair of electrodes on a common substrate lie within a reaction space defined by a set of insulating walls, effecting both cell lysis that releases nucleic acids and controlled fragmentation of the nucleic acids thus released.

Lysis electrodes may have a variety of geometries and arrangements. In some embodiments lysis electrodes are mounted on or form part of an interior surface of a chamber or channel used for lysis (a "lysis zone"). One embodiment is shown in FIG. 1, where one lysis electrode (110) is separated from a second lysis electrode (120) by an insulator (130). The space between the electrodes (140) is occupied, at least in part, by biological sample during lysis and fragmentation. Another embodiment of the inventive subject matter is shown in FIG. 2, where lysis electrodes (210, 220) lie on an insulating substrate (250) that is exposed to fluid containing a biological sample. In such an embodiment, insulating walls (230) may be used to define a flow channel, and may be further augmented by the addition of an insulating wall (260) that forms a chamber (240).

Figure 3:
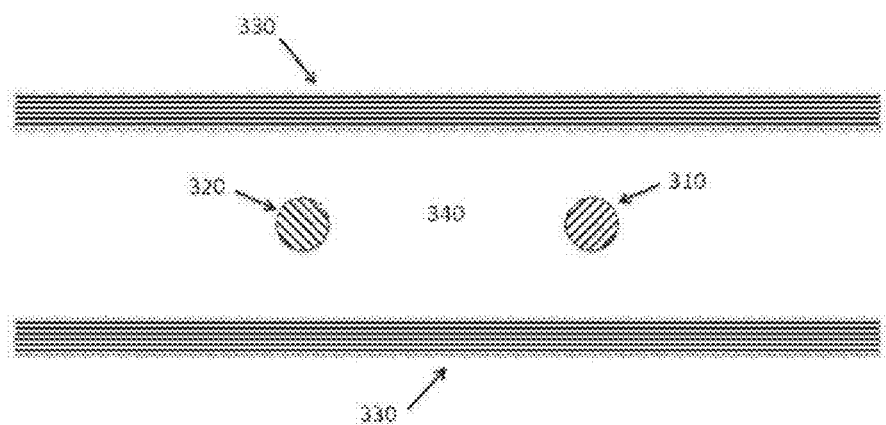
FIG. 3 schematically depicts another embodiment of an extraction zone of the inventive subject matter. A pair of electrodes lies within an insulated channel which serves as a reaction space. The electrode pair effect both cell lysis that releases nucleic acids and controlled fragmentation of the nucleic acids thus released.
Figure 4:
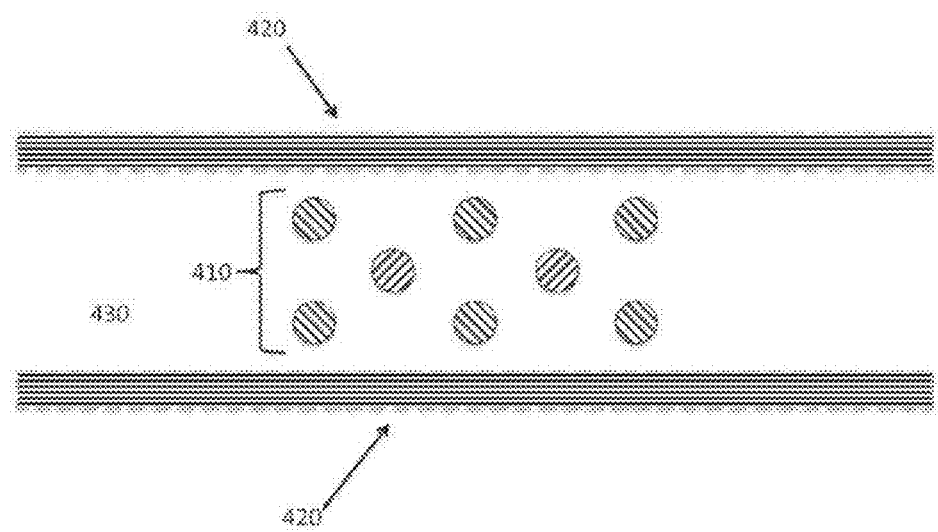
FIG. 4 schematically depicts another embodiment of an extraction zone of the inventive subject matter. An array of electrodes lies within an insulated channel which serves as a reaction space. The array of electrodes effects both cell lysis that releases nucleic acids and controlled fragmentation of the nucleic acids thus released.

In other embodiments, lysis electrodes may lie within the interior space of a chamber or channel. For example, FIG. 3 shows a lysis chamber or lysis zone with linear electrodes (310, 320) that lie within a chamber or channel (340) bounded by insulated walls (330). Such a chamber or channel could be constructed as a serpentine, and configured to utilize either a flowing or static sample. FIG. 4 illustrates a similar embodiment that utilizes an array of micro-structured electrodes (410) that are placed in a lysis zone bounded by insulators (420) to form a chamber or channel (430) containing a biological sample. In such an embodiment the electrodes may be formed on a planar surface by suitable means (including, for example, micromachining, molding, plating, and electrodeposition) and may be configured such that the gap between the electrodes is larger than the diameter of an individual electrode.

Figure 5:
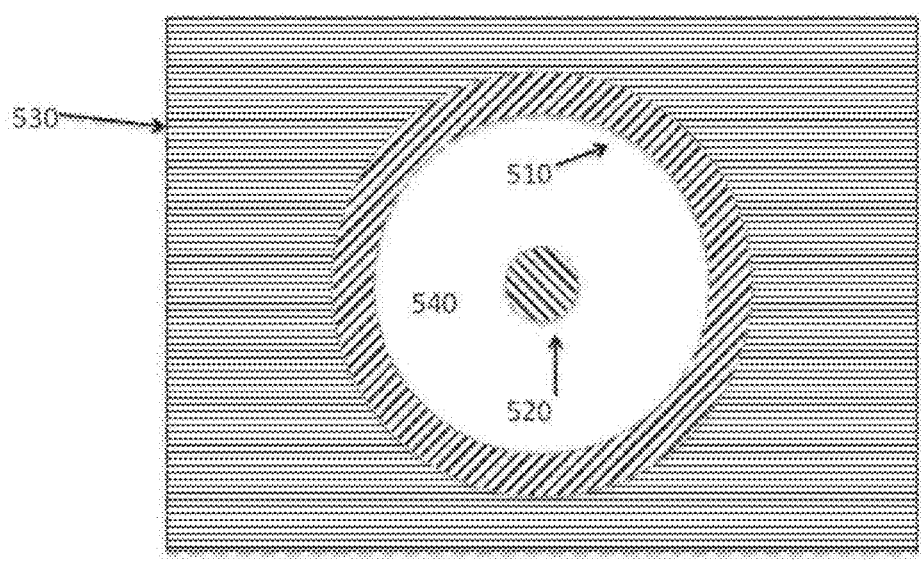
FIG. 5 schematically depicts another embodiment of an extraction zone of the inventive subject matter. An electrode pair is imbedded in an insulating matrix. One member of the pair is cylindrical. The remaining electrode lies within the lumen of the cylindrical electrode, which also defines reaction space within which the electrode pair effects both cell lysis that releases nucleic acids and controlled fragmentation of the nucleic acids thus released.

In other embodiments, the lysis zone is essentially tubular. One such embodiment is shown in FIG. 5, where one lysis electrode (510) is a hollow tube forming the outer wall of a chamber (540) containing a biological sample and a second lysis electrode (520) lies within the lumen of the tubular electrode (510). The outermost lysis electrode (510) may be surrounded by or embedded in an insulator (530) in such an embodiment. Such an embodiment can be used with either a static or flowing sample.

Figure 6:
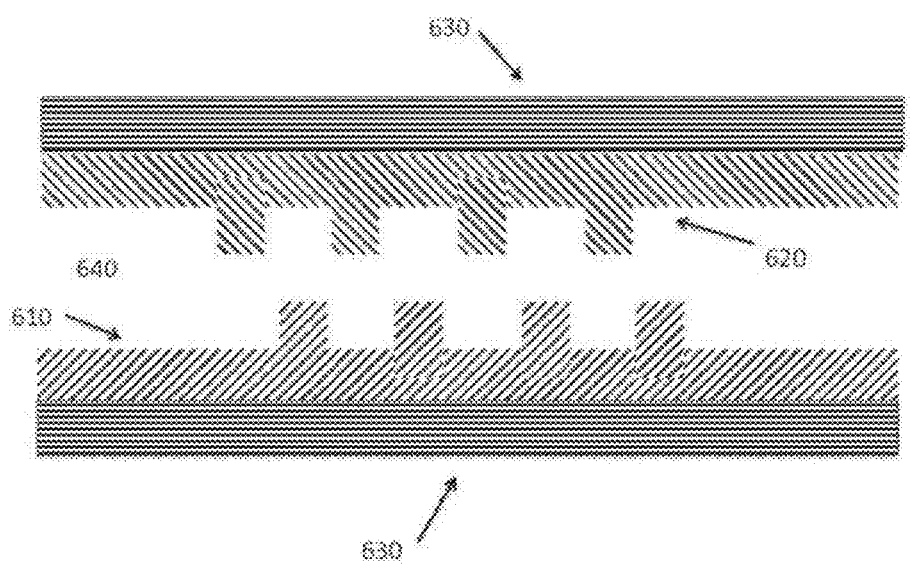
FIG. 6 schematically depicts another embodiment of an extraction zone of the inventive subject matter. Individual electrodes of an electrode pair are attached to insulating substrates that are mounted in parallel, the space between defining a reaction space within which the electrode pair effects both cell lysis that releases nucleic acids and controlled fragmentation of the nucleic acids thus released. The electrodes include features that project into the reaction space.
Figure 7:
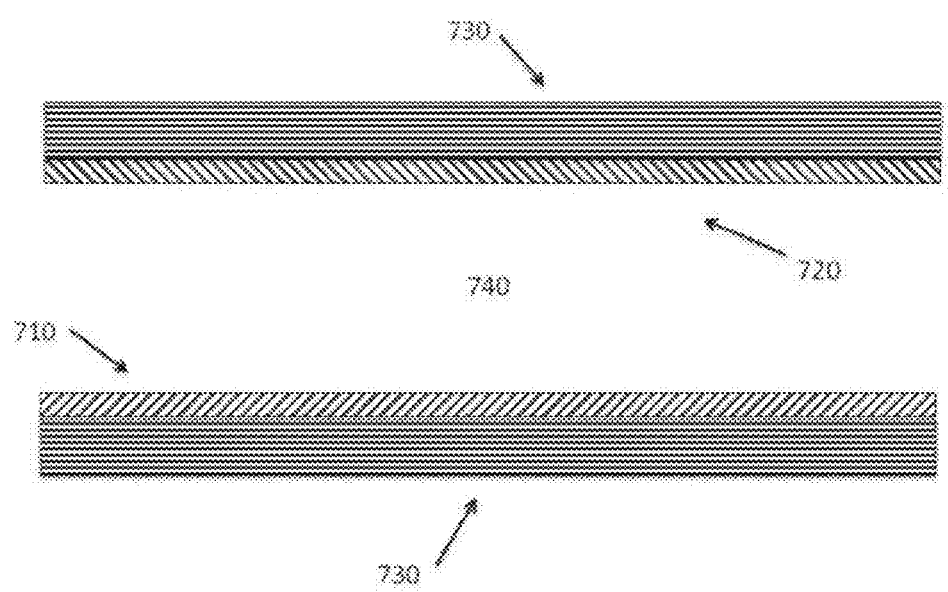
FIG. 7 schematically depicts another embodiment of an extraction zone of the inventive subject matter. Individual electrodes of an electrode pair are attached to insulating substrates that are mounted in parallel, the space between defining a reaction space within which the electrode pair effects both cell lysis that releases nucleic acids and controlled fragmentation of the nucleic acids thus released.

In some embodiments, the lysis zone is configured as a channel containing lysis electrodes. FIG. 6 illustrates such an embodiment, where a channel (640) includes a pair of lysis electrodes (620, 610) that include ridges or projections that protrude into the channel. These serve to increase local field strength applied to a biological sample within the channel (640) and, in the case of a flowing stream of fluid sample, serve to cause turbulence that improves mixing. Such ridges or projections may be produced by molding, micromachining, electrodeposition of microstructured materials, or any suitable means. In an alternative embodiment, FIG. 7 shows a channel (740) that includes a pair of lysis electrodes (710, 720) that are configured as a set of rails that lie the edge of the insulating walls (730) of the channel. In such embodiments, the biological sample may be present in a fluid that flows along the channel or that lies static within the channel.

Figure 8:
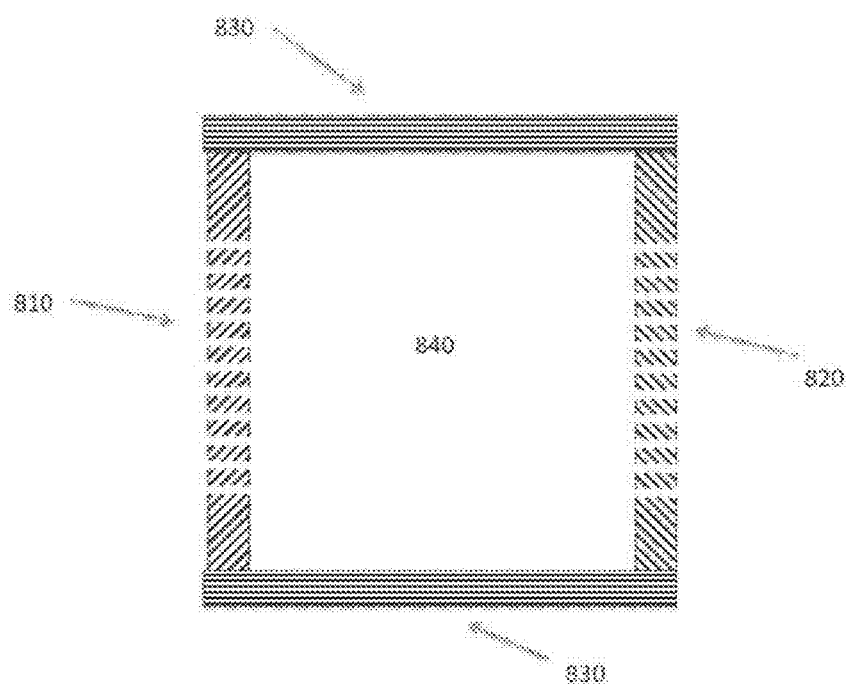
FIG. 8 schematically depicts another embodiment of an extraction zone of the inventive subject matter. A set of porous electrodes form two walls of a reaction space, which is further defined by a pair of insulating walls. Within the reaction space the electrode pair effects both cell lysis that releases nucleic acids and controlled fragmentation of the nucleic acids thus released.

In yet another embodiment, as shown in FIG. 8, the lysis electrodes (810, 820) are permeable to liquids and are separated by an insulator (830), so that a fluid containing the biological sample within the space (840) that lies between the electrodes may be lysed and fragmented. The biological sample may be present in a fluid that flows through the lysis electrodes or that lies static between the lysis electrodes. In such an embodiment the lysis electrodes may be porous, woven, in the form of a mesh or web, or a combination of these, and may also serve as a filtration medium.

Figure 9:
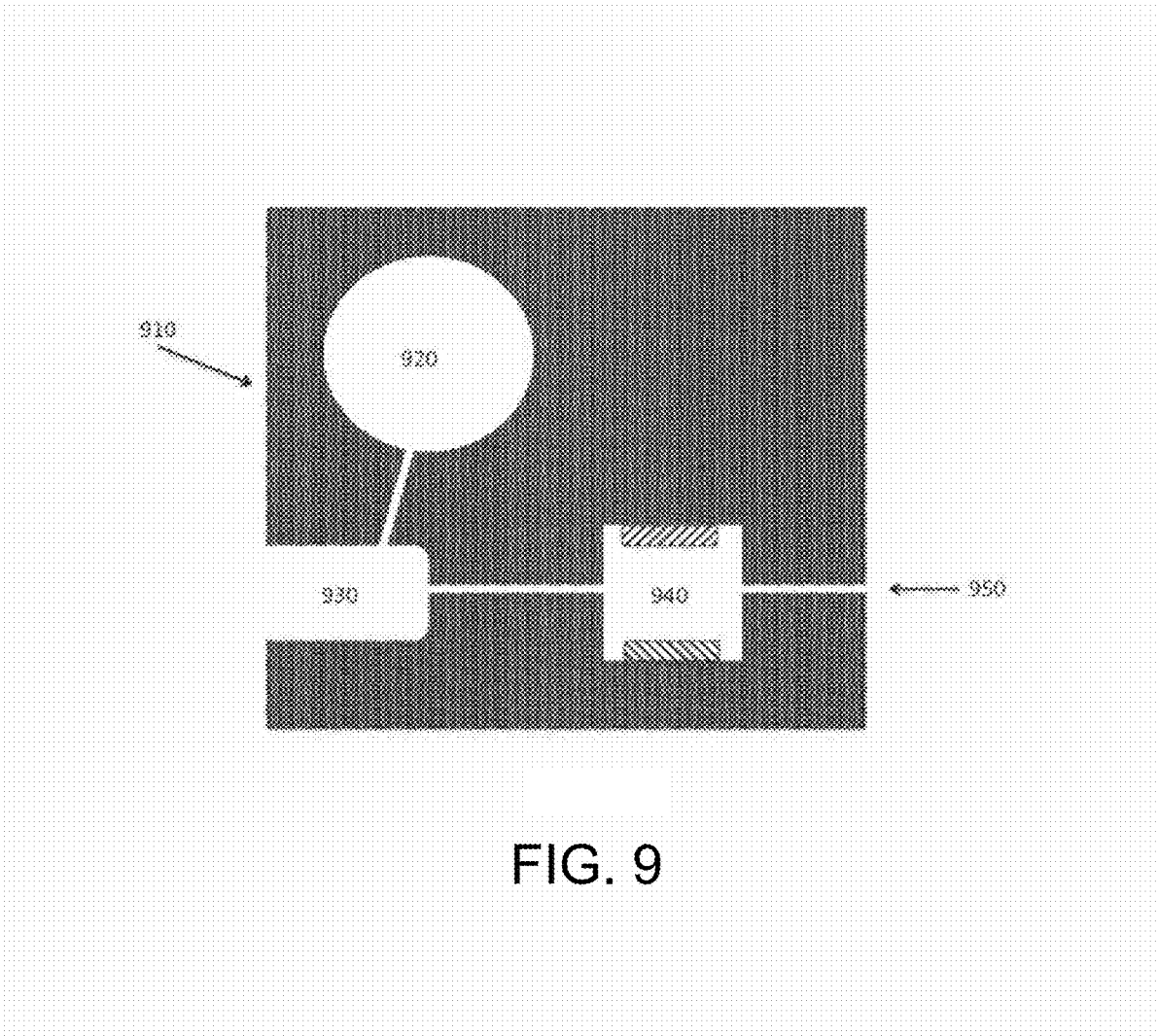
FIG. 9 schematically depicts an embodiment of a device of the inventive subject matter. A reagent reservoir, sample receiving area, and extraction zone are provided on a single substrate. The sample receiving area is configured to receive the collecting portion of a sample collector, lies between the reagent reservoir and the extraction zone, and is in fluid communication with both.

The lysis electrode and lysis zone embodiments described above may be incorporated into a cartridge. Such a cartridge may prepare a sample for subsequent analysis; such a preparative cartridge may, for example, be configured to remove a portion of a biological sample from a sample collector or swab and transport it to a lysis zone where biological compartments are lysed and released analytes fragmented. In such an embodiment, the biological sample may include the contents of an eluted swab in buffer, blood, plasma, serum, cerebral spinal fluid, urine, feces, seminal fluid, mucus, tissue, respiratory fluids, food, water, air, eluted contents of a filter or urogenital secretions. An example of a preparative cartridge is shown in FIG. 9, where a substrate (910) supports a fluid reservoir (920) that is in fluid communication with a sample receiving area or zone (930), which is in turn in fluid communication with a lysis chamber or zone (940) that includes a pair of lysis electrodes. A flow of fluid, which can include reagents that enhance the lysis and fragmentation functions of the device, from the fluid reservoir transports a portion of the biological sample in the sample receiving zone (930) to the lysis zone (940). The fluid reservoir (920) may include a pliant or flexible wall, so that pressure applied to the outer surface of such a wall reduces the internal volume of the fluid reservoir and induces flow towards the sample receiving zone. Following lysis and fragmentation, the prepared sample can exit the cartridge via an outlet (950).

Figure 10:
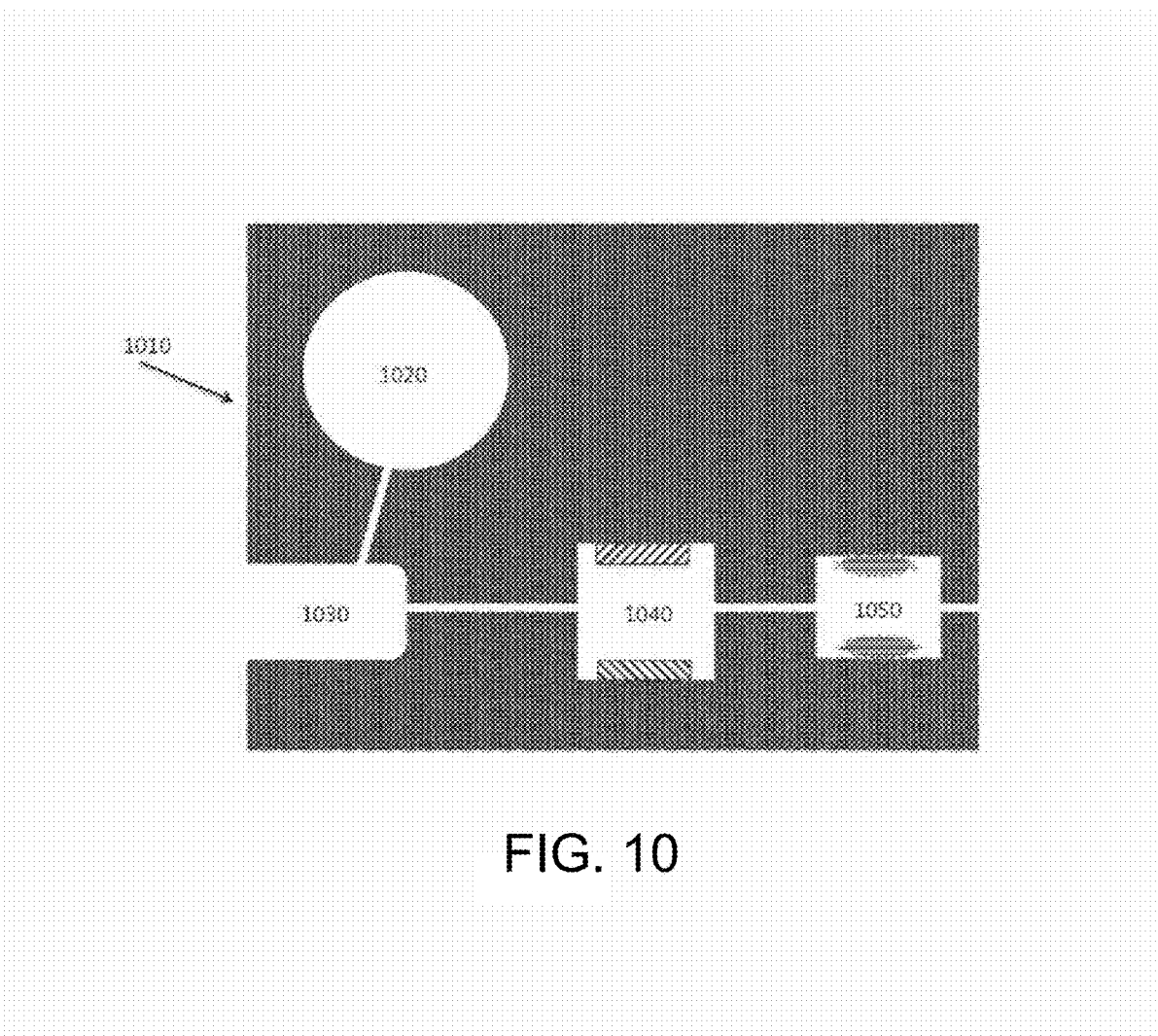
FIG. 10 schematically depicts an embodiment of a device of the inventive subject matter. A reagent reservoir, sample receiving area, extraction zone, and analysis zone are provided on a single substrate. The sample receiving area is configured to receive the collecting portion of a sample collector, lies between the reagent reservoir and the extraction zone, and is in fluid communication with both. A fluid channel directs materials from the extraction zone to the analysis zone.

In other embodiments, a cartridge may be configured to include areas suitable to both prepare a biological sample and characterize the resulting prepared sample, thereby providing a sample-to-answer cartridge. An example of a sample-to-answer cartridge is shown in FIG. 10. Here, a substrate (1010) supports a fluid reservoir (1020) that is in fluid communication with a sample receiving area or zone (1030), which is in turn in fluid communication with a lysis chamber or zone (1040) that includes a pair of lysis electrodes. A flow of fluid, which can include reagents that enhance the lysis and fragmentation functions of the device, from the fluid reservoir transports a portion of the biological sample in the sample receiving zone (1030) to the lysis zone (1040). The fluid reservoir (1020) may include a pliant or flexible wall, so that pressure applied to the outer surface of such a wall reduces the internal volume of the fluid reservoir and induces flow towards the sample receiving zone. Following lysis and fragmentation, the prepared sample moves to an analysis chamber or zone (1050) that is in fluid communication with the lysis chamber or zone (1040), where it is characterized. Such an analysis zone may include a sensing electrode and a reference electrode for use in electrochemical detection of analytes. In some embodiments, the analysis zone of the analysis cartridge may utilize a lysis electrode of the lysis zone of the preparation cartridge as a reference electrode. In other embodiments, a single chamber or flow channel may include both lysis electrodes and sensing and reference electrodes. In still another embodiment, a single chamber or flow channel may include lysis electrodes and a sensing electrode, where a lysis electrode serves as a reference electrode for analyte characterization.

Figure 11:
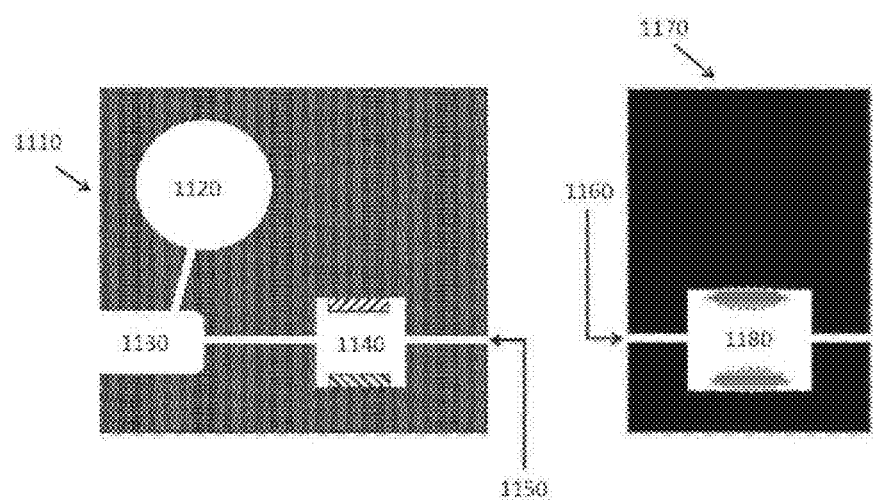
FIG. 11 schematically depicts an embodiment of a device of the inventive subject matter. A reagent reservoir, sample receiving area, and extraction zone are provided on one substrate. The sample receiving area is configured to receive the collecting portion of a sample collector, lies between the reagent reservoir and the extraction zone, and is in fluid communication with both. A fluid channel leads from the extraction zone. An analysis zone with a complementary fluid channel is provided on a second substrate.

In an alternative embodiment a sample preparation cartridge and an analysis cartridge may be provided as separate units that are brought into fluid communication to form a sample-to-answer device. This arrangement advantageously permits alternate configurations and easily customizable devices wherein a sample preparation cartridge may be coupled to different types of analytical cartridges to facilely produce sample-to-answer devices with different functions or specificities. FIG. 11 illustrates such an embodiment, where the sample preparation portion includes a substrate (1110) that supports a fluid reservoir (1120) that is in fluid communication with a sample receiving area or zone (1130), which is in turn in fluid communication with a lysis chamber or zone (1140) that includes a pair of lysis electrodes. A flow of fluid, which can include reagents that enhance the lysis and fragmentation functions of the device, from the fluid reservoir transports a portion of the biological sample in the sample receiving zone (1130) to the lysis zone (1140). The fluid reservoir (1120) may optionally include a pliant or flexible wall, so that pressure applied to the outer surface of such a wall reduces the internal volume of the fluid reservoir and induces flow towards the sample receiving zone. The prepared sample exits the lysis zone via a prepared sample outlet (1150), which may be brought into fluid communication with the prepared sample inlet (1160) of the analysis cartridge. The analysis cartridge includes a second substrate (1170) that supports a prepared sample inlet (1160) that is in fluid communication with an analysis zone (1180) that may include a sensing electrode and a reference electrode for use in electrochemical detection of analytes. In some embodiments, the analysis zone of the analysis cartridge may utilize a lysis electrode of the lysis zone of the preparation cartridge as a reference electrode.

In still another embodiment, a sample-to-answer cartridge is provided in which the prepared sample is distributed to two or more analysis zones. This arrangement advantageously permits a variety of characterizations to be performed on a single biological sample applied to the cartridge. For example, both immunochemical and nucleic acid characterizations may be performed from the same biological sample on the same cartridge. Alternatively, analysis zones may be configured to perform different nucleic acid characterization, permitting detection of multiple genetic markers from a single biological sample on the same cartridge. In another embodiment, one analysis zone may serve as a reference analysis zone. In such an embodiment, the reference analysis zone may be configured for characterization of an analyte that has been introduced into the biological sample or that is known to be present. The result of such a characterization may be used to "scale" the result of a characterization of a second analyte (in a second analysis zone) that is present in unknown quantities, thereby providing a degree of correction for performance of the particular device and/or reagents.

Figure 12:
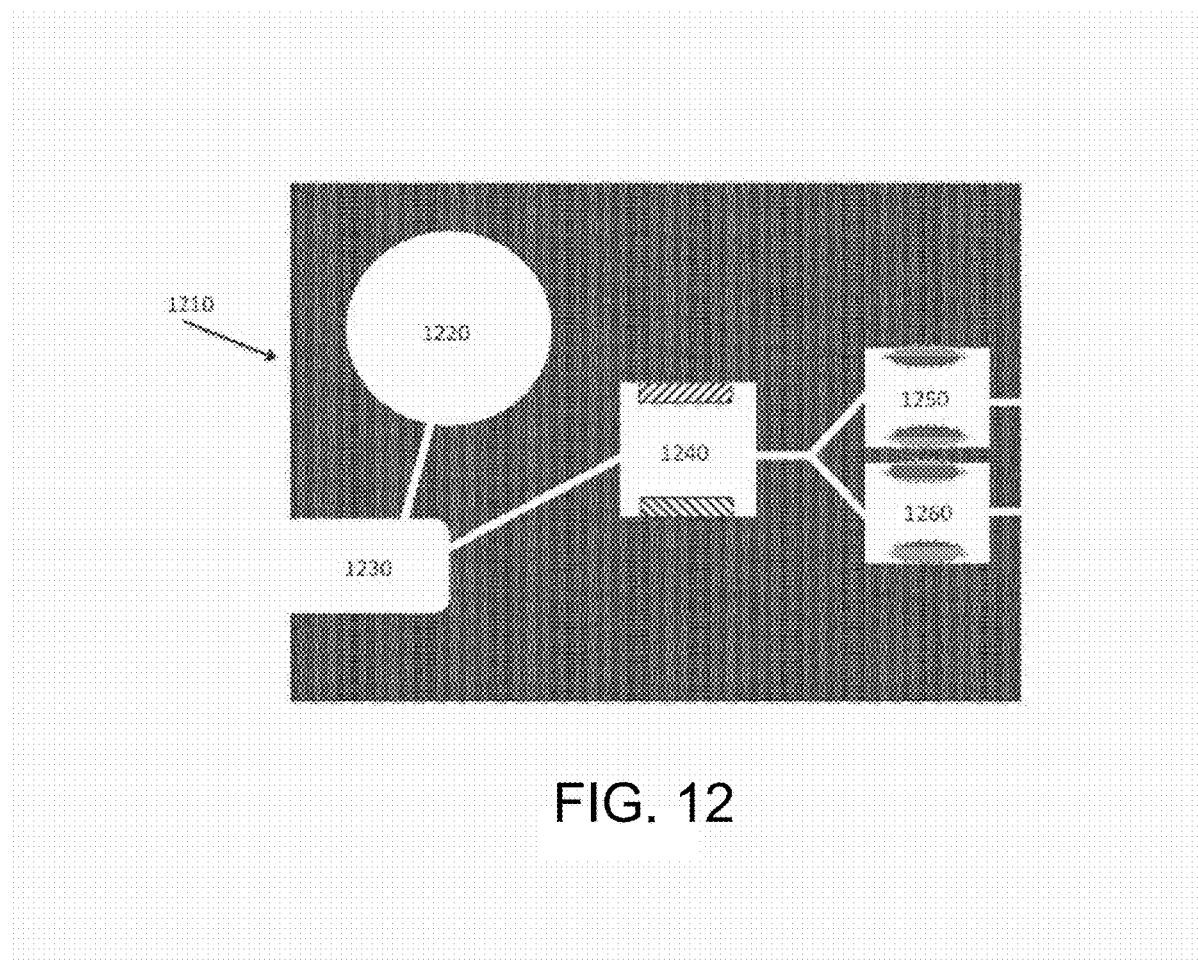
FIG. 12 schematically depicts an embodiment of the device of the inventive subject matter. A reagent reservoir, sample receiving area, extraction zone, and a plurality of analysis zones are provided on a single substrate. The sample receiving area is configured to receive the collecting portion of a sample collector, lies between the reagent reservoir and the extraction zone, and is in fluid communication with both. A branched fluid channel directs and distributes material from the extraction zone to the analysis zones.

Another example of an embodiment with a plurality of analysis zones is shown in FIG. 12. Here, a substrate (1210) supports a fluid reservoir (1220) that is in fluid communication with a sample receiving area or zone (1230), which is in turn in fluid communication with a lysis chamber or zone (1240) that includes a pair of lysis electrodes. A flow of fluid, which can include reagents that enhance the lysis and fragmentation functions of the device, from the fluid reservoir transports a portion of the biological sample in the sample receiving zone (1230) to the lysis zone (1240). The fluid reservoir (1220) may include a pliant or flexible wall, so that pressure applied to the outer surface of such a wall reduces the internal volume of the fluid reservoir and induces flow towards the sample receiving zone. Following lysis and fragmentation, the prepared sample moves through a branched fluid channel and is distributed to two analysis zones (1250, 1260), where it is characterized. Each analysis zone may include a sensing electrode and a reference electrode for use in electrochemical detection of analytes. Analysis zones may be configured to perform different characterizations. In such an embodiment, multiple analysis zones can be configured to utilize a single reference electrode and/or counter electrode. In an alternative embodiment, analysis zones may utilize a lysis electrode of the type previously described in the lysis zone of the preparation cartridge as a reference electrode or counter electrode. In other embodiments a single chamber or flow channel may include both lysis electrodes and sensing and reference electrodes. In still another embodiment, a single chamber or flow channel may include lysis electrodes and sensing electrodes, where a lysis electrode serves as a reference electrode for analyte characterization.

In some embodiments of the inventive subject matter, secondary reagent reservoirs are provided that permit the addition of reagents necessary for processes occurring downstream from these reservoirs. Reagents may be supplied as liquids held within the reagent reservoirs but may also be supplied as dry reagents that are present in fluid pathways, and are reconstituted when flow of a liquid buffer from an upstream reservoir is established. Alternatively, reagents may be supplied as dry reagents stored with a reagent reservoir. In such an embodiment, dry reagents would be reconstituted when the user adds liquid, such as buffer or water, to such a reagent reservoir prior to use.

Fluid pathways of the contemplated devices may include valves to direct and control the flow of fluid. For example, in a device in which flow is established by applying pressure to a pliant wall that forms part of a reagent reservoir one or more one-way valves may be incorporated into the fluid paths of the device to insure that flexion of the pliant wall on release of pressure does not reverse the direction of flow. In other embodiments fluid pathways may include bubble trapping features, for example incorporating a serpentine path in communication with gas permeable membranes or vents. In some embodiments chambers within the device, for example a lysis zone or an analysis zone, may include features that permit verification of an effective level of fluid (e.g., sufficient to come into contact with the electrodes) within the chamber. For example, a lysis zone and an analysis zone may be constructed, at least in part, of transparent or translucent materials that permit noninvasive optical monitoring of the fluid levels within.

As noted above, the analysis zone may be configured to perform electrochemical detection. In such embodiments, the analysis zone includes a sensing electrode and a reference electrode. In use, a biasing current or charge is applied to the sensing electrode and the reference electrode. Upon addition of prepared sample, changes in the resulting current or charge is measured to characterize the prepared sample. Such sensing electrodes may be nanostructured, as disclosed in US2011/0233075, which is incorporated by reference herein. The nanostructures of the sensing electrode may be rough, spiky, or fractal. Such a sensing electrode may also include a reporting system that is responsive to a biomolecular stimulus. For example, a reporting system could include a probe molecule that is responsive to protein: protein interactions or to nucleic acid hybridization. Such probe molecules include, but are not limited to, nucleic acids, peptide nucleic acids, morpholino nucleic acid analogs, locked nucleic acids, immunoglobulins, proteins, and peptides. For example, in characterization of a target nucleic acid from a sample, a probe molecule may include a sequence that is at least partially complementary to the target nucleic acid's sequence. In another example, in characterization of an antigen from a sample, a probe molecule may include a monoclonal antibody specific for the antigen. A reporting system may also include tethering portions with chemical groups, such as thiols, that facilitate attachment to the sensing electrode. A reporting system may also include an electrocatalytic reporter, such as ruthenium hexamine, potassium ferricyanide, or combinations thereof. Such reporting systems may provide sufficient sensitivity to directly detect unamplified genetic material from a processed biological sample.

Figure 13:
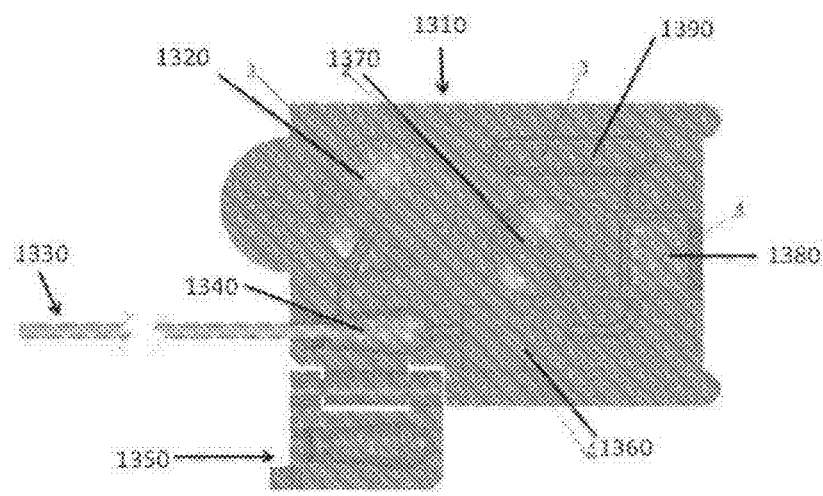
FIG. 13 depicts an embodiment of the device of the inventive subject matter. Multiple reagent reservoirs, a sample receiving area configured to engage a sample collector, an extraction zone, an analysis zone, and a waste collection zone are provided on a single substrate. The device is shown engaging a sample swab.

FIG. 13 shows a sample swab and a preferred embodiment of a sample-to-answer cartridge. A substrate (1310) supports a fluid reservoir (1320) that is in fluid communication with a sample receiving zone (1340). The biological sample is shown being applied on the collection tip of a sample collector (1330), which lies within the sample receiving zone (1340), which may be closed using a sample cover (1350). Closing the sample cover both secures the sample applicator and defines a sample chamber that assists in directing the flow of fluid from the fluid reservoir (1320) and through the collection tip of the sample collector (1330), thereby transferring a portion of the biological sample to the lysis zone (1360). Following lysis and fragmentation at least a portion of the prepared sample is transferred to the analysis zone (1380); secondary reagents from a secondary reagent reservoir (1370) may be added at this time. Waste materials are collected in a waste reservoir (1390) as the biological sample is prepared and characterized.

There are a number of formats, materials, and size scales that may be used in the construction of the sample preparation and sample analysis cartridges described herein. Some embodiments are constructed, at least in part, as microfluidic devices. In such embodiments, the reagent reservoirs, lysis zones, analysis zones, and the connecting fluid channels may be comprised of PDMS (or similar polymers), and fabricated using soft lithography.

In some embodiments, single layer devices are contemplated. In other embodiments multilayer devices are contemplated.

Other methods of fabrication are of single and multilayer devices are, but not limited to, micromachining of bulk solid, use of pressure sensitive adhesives with channel structures cut and subsequently laminated, injection molded, overmolded, thermo formed or hot embossed structures, or any other method that is used in manufacture of microfluidic or larger structures known to those skilled in the art.

Examples

Figures 14A, 14B, 14C:
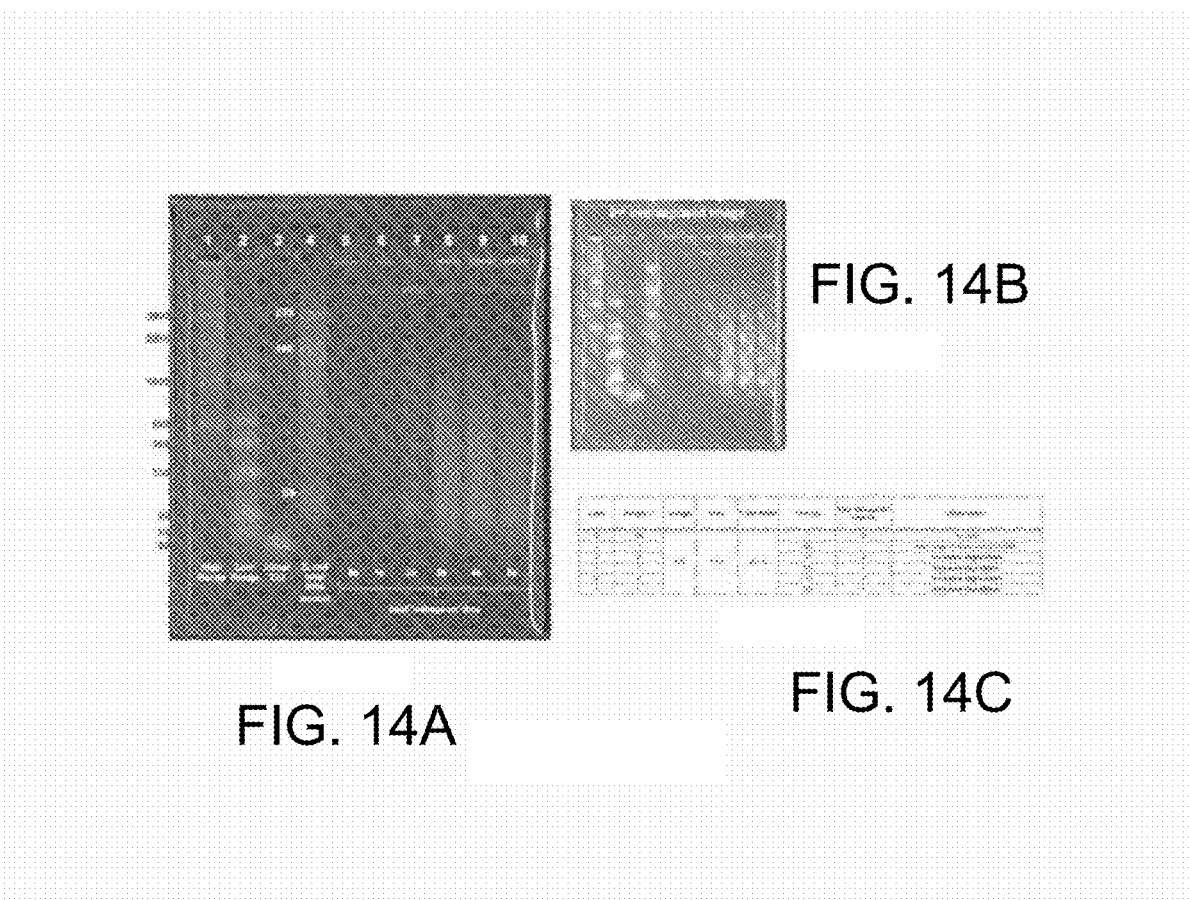
FIG. 14A shows a stained agarose gel. Lanes 1, 2 and 3 contain size standards; lane 5 contains the biological sample prior to treatment; lanes 6 through 10 show samples representing different time points during treatment.
FIG. 14B shows a longer exposure of the gel of FIG. 14A.
FIG. 14C provides a summary of experimental conditions.

Lysis and Fragmentation. A suspension of *Escherichia coli* was prepared in nuclease-free PBS and introduced into a processing zone containing a pair of lysis electrodes. A 40V potential was applied to the lysis electrodes as 40 millisecond pulses at a frequency of 1 Hz. Samples were prepared at various time intervals and applied to a 2% agarose gel prepared with 1×TBE, along with appropriate size standards, then stained with SYBR Gold and imaged. Results are shown in FIG. 14. FIG. 14A shows a normal exposure of the gel; FIG. 14B shows the same gel that has been overexposed in order to reveal detail. Lanes 1 and 2 contain high and low molecular weight standards (respectively), lane 3 contains a representative 20 mcr oligo, and lane 4 contains a total *E. coli* RNA control. A sample taken prior to the application of voltage to the lysis electrodes was placed in lane 5, which does not show significant material entering the gel. Lanes 6 through 10 show the effect of voltage applied to the lysis electrodes for 25, 50, 75, 100 and 125 seconds from the initiation of voltage. These devices were run with 40 ms pulse width and a frequency of 1 Hz. Lanes 6-10 equate to a cumulative applied voltage of 1, 2, 3, 4 and 5 s respectively. Significant release of high molecular weight RNA is apparent with as little as 1 second of applied voltage to the lysis electrodes. Release of additional RNA and fragmentation of the RNA so released is apparent after as little as two seconds, with the steady accumulation of RNA fragments of less than about 500 bases in length and an accompanying loss of high molecular weight RNA as the total applied voltage increases to 5 seconds. FIG. 14C provides a key for the experimental lanes of the gel.

Figure 15:
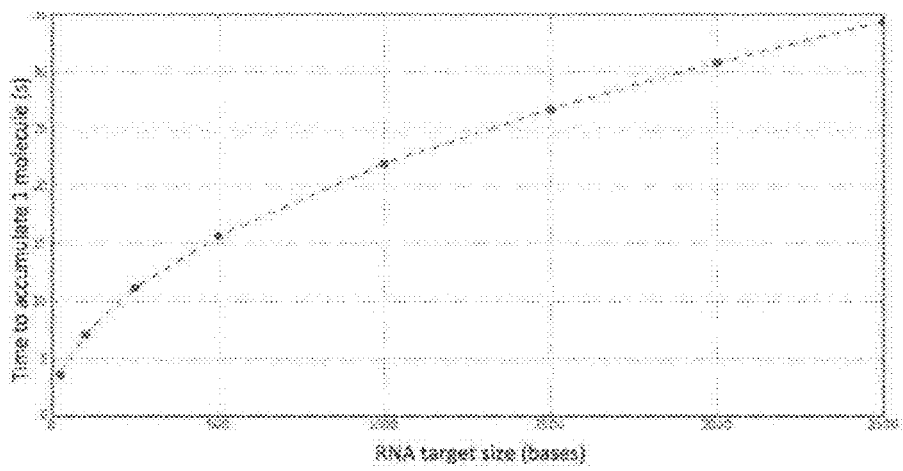
FIG. 15 is a graph depicting the effect of nucleic acid fragment size on the time required for analysis.

Effects of RNA Fragmentation. A simulation was performed to determine the effect of reduction in RNA analyte size due to fragmentation on the time required for sample analysis. The time required to accumulate a molecule of RNA on a sensing electrode was calculated as a function of the size of the target RNA present in a processed sample. Results are shown in FIG. 15. Reduction in the size of the analyte RNA from 2000 bases to 500 bases or less in length reduces the time required to accumulate, and therefore analyze, the analyte RNA by 50% or more.

Thus, specific embodiments and applications of methods and devices for sample preparation and analysis have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A device for analyzing a biological sample, the device comprising:
   a sample receiving zone configured to receive a biological sample, the biological sample including nucleic acids;
   a sample extraction zone in fluid communication with the sample receiving zone and configured to receive the biological sample from the sample receiving zone, the sample extraction zone including a plurality of electrodes in electrical communication with an electrical source and configured to fragment the nucleic acids into a plurality of fragmented nucleic acids when a first electrical signal is applied to the plurality of electrodes;
   a signal control unit configured to determine an overall treatment time of the first electrical signal applied to the plurality of electrodes based on a desired average length in bases of the plurality of fragmented nucleic acids; and
   a sample analysis zone in fluid communication with the sample extraction zone and including a sensing electrode and a reference electrode for analyzing the biological sample.

2. The device of claim 1, further comprising:
   a fluid reservoir including a pliant wall defining an interior volume, the pliant wall having an external surface configured such that pressure applied to the external surface of the pliant wall results in deformation of the pliant wall into an interior volume of the fluid reservoir, thereby inducing fluid flow through the sample receiving zone.

3. The device of claim 2, wherein the fluid reservoir includes an extraction buffer.

4. The device of claim 1, further comprising:
   a flow channel, wherein each of the plurality of electrodes extends along a length of the flow channel, and wherein each of the plurality of electrodes comprises ridges or projections that protrude into the flow channel.

5. The device of claim 1, wherein each of the plurality of electrodes is disposed in the extraction zone and configured to effect release of a plurality of nucleic acids from the biological sample and to effect fragmentation of the plurality of nucleic acids.

6. The device of claim 1, wherein the sample receiving zone is configured to receive and retain the biological sample and at least a portion of a sample collecting device.

7. The device of claim 1, wherein the sensing electrode includes a probe molecule that is at least partially complementary to the fragmented nucleic acid.

8. The device of claim 7, wherein the sample analysis zone includes a reporter system that is responsive to nucleic acid hybridization to the probe molecule.

9. The device of claim 8, wherein the sensing electrode includes a nanostructured microelectrode, wherein the nanostructured microelectrode is at least one of textured and fractal.

* * * * *

UNITED STATES PATENT AND TRADEMARK OFFICE
CERTIFICATE OF CORRECTION

PATENT NO. : 10,301,666 B2
APPLICATION NO. : 15/408225
DATED : May 28, 2019
INVENTOR(S) : Kelley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 152 days.

Signed and Sealed this
Tenth Day of January, 2023

Katherine Kelly Vidal
*Director of the United States Patent and Trademark Office*